(12) United States Patent
Lang et al.

(10) Patent No.: US 8,309,312 B2
(45) Date of Patent: Nov. 13, 2012

(54) MEANS FOR DETECTION AND PURIFICATION OF CD8+ T LYMPHOCYTE POPULATIONS SPECIFIC TO PEPTIDES PRESENTED IN THE CONTEXT OF HLA

(75) Inventors: Francois Lang, Nantes (FR); Marie Bodinier, Nantes (FR); Francois Davodeau, Nantes (FR); Marc Bonneville, Vertou (FR)

(73) Assignee: Institut National de la Sante et de la Recherche (FR)

( * ) Notice: Subject to any disclaimer, the term of this patent is extended or adjusted under 35 U.S.C. 154(b) by 0 days.

(21) Appl. No.: 12/571,942

(22) Filed: Oct. 1, 2009

(65) Prior Publication Data

US 2010/0105077 A1 Apr. 29, 2010

Related U.S. Application Data

(60) Continuation of application No. 10/765,097, filed on Jan. 28, 2004, now abandoned, which is a division of application No. 09/831,019, filed as application No. PCT/FR00/02443 on Sep. 5, 2000, now abandoned.

(30) Foreign Application Priority Data

Sep. 6, 1999 (FR) .................................... 99 11133

(51) Int. Cl.
*G01N 33/53* (2006.01)
*A01N 63/00* (2006.01)
(52) U.S. Cl. .......................... 435/7.2; 435/7.24; 435/7.8
(58) Field of Classification Search .......................... None
See application file for complete search history.

(56) References Cited

U.S. PATENT DOCUMENTS 5,635,363 A 6/1997 Altman et al.

FOREIGN PATENT DOCUMENTS

| WO | WO 96/26962 A1 | 9/1996 |
| WO | WO 97/44667 A2 | 11/1997 |
| WO | WO 99/11775 A1 | 3/1999 |

OTHER PUBLICATIONS

Neveu et al (International Immunol. 2006, 18(7): 1139-1145).*
Gostick et al (Eur. J. Immunol. 2007, 37(2) : 479-486).*
Altman, J.D., et al., "Phenotypic Analysis of Antigen-Specific T Lymphocytes," *Science 274*: 94-96, American Association for the Advancement of Science, United States (1996).
Bodinier, M., et al., "Efficient detection and immunomagnetic sorting of specific T cells using multimers of MHC class I and peptide with reduced CD8 binding," *Nature Medicine 6*:707-710, Nature Publishing Company, United States (2000).
Chun, T-W., et al.,"Suppression of HIV replication in the resting $CD4^+$ T cell reservoir by autologous $CD8^+$ T cells: Implications for the development of therapeutic strategies," *Proc. Natl. Acad. Sci. 98*: 253-258, National Academy of Sciences, United States (2001).
Couedel, C., et al., "Selection and Long-Term Persistence of Reactive CTL Clones During an EBV Chronic Response Are Determined by Avidity, CD8 Variable Contribution Compensating for Differences in TCR Affinities," *J.Immunol. 162*: 6351-6358, American Association of Immunologists, United States (1999).
Gao, G.F., et al., "Crystal structure of the complex between human $CD8\alpha\alpha$ and HLA-A2," *Nature 387*:630-634, Nature Publishing Group, England (1997).
Garboczi, D.N., et al., "HLA-A2-Peptide complexes: Refolding and crystallization of molecules expressed in *Escherichia coli* and complexed with single antigenic peptides," *Proc. Natl. Acad. Sci. 89*: 3429-3433, National Academy of Sciences, United States (1992).
Luxembourg, A.T., et al., "Biomagnetic isolation of antigen-specific CD8+ T cells usable in immunotherapy," *Nature Biotechnology 16*: 281-285, Nature American Publishing, United States (1998).
Missale, G., et al., "HLA-A31- and HLA-Aw68-restricted Cytotoxic T cell Responses to a Single Hepatitis B Virus Nucleocapsid Epitope during Acute Viral Hepatitis," *J. Exp. Med.177*: 751-762, Rockefeller University Press, United States (1993).
Ogg, G.S. & McMichael, A.J., "HLA-peptide tetrameric complexes," *Curr. Opin. Immunol.10*: 393-396, Elsevier, England (1998).
Salter, R.D., et al., "A binding site for the T-cell co-receptor CD8 on the $\alpha_3$ domain of HLA-A2," *Nature 345*:41-46, Nature Publishing Group, England (1990).
Schwartz, M. & Kipnis, J., "Multiple Sclerosis as a By-Product of the Failure to Sustain Protective Autoimmunity: A Paradigm Shift," *The Neuroscientist 8*: 405-413, Sage Publications, United States (2002).
Salter et al., "Polymorphism in the $\alpha_3$ domain of HLV-A molecules affects binding to CD8.", *Letters to Nature*, vol. 338, Mar. 23, 1989, pp. 345-347.

* cited by examiner

*Primary Examiner* — Michael Szperka
*Assistant Examiner* — Marianne Dibrino
(74) *Attorney, Agent, or Firm* — Merchant & Gould, P.C.

(57) ABSTRACT

The invention concerns multimers developed from recombinant proteins analogues of MHC class I.

14 Claims, 7 Drawing Sheets

CD3 marking

FIGURE 4C mutated Bmlf1/A2 tetramer marking

Ratio of mutated tetramer AFI /CD3 AFI

Marking before screening

FIGURE 6

Marking after screening with normal A2/pp65 tetramer

Marking after screening with mutated A2/pp65 tetramer

FIGURE 7

Patient 1

Patient 2

MEANS FOR DETECTION AND PURIFICATION OF CD8+ T LYMPHOCYTE POPULATIONS SPECIFIC TO PEPTIDES PRESENTED IN THE CONTEXT OF HLA

The present application is a continuation of application Ser. No. 10/765,097, filed Jan. 28, 2004, now abandoned, which is a divisional of application Ser. No. 09/831,109, filed Jul. 17, 2001, now abandoned, which is a 371 U.S. national phase of International Application No. PCT/FR00/02443, filed Sep. 5, 2000, which designated the U.S., the entire contents of which are incorporates herein by reference.

FIELD OF THE INVENTION

The invention relates to means for detection and purification of CD8+ T lymphocyte populations specific to peptides presented in the context of HLA.

BACKGROUND OF THE INVENTION

The T lymphocyte carries a receptor specific to the antigen against which it is directed, called TCR. This TCR is composed of several chains, the $\alpha$ and $\beta$ chains of which are involved in the specific recognition of a particular antigenic peptide presented in an HLA molecule. This recognition is shown by the ability of the $\alpha/\beta$ TCR of the T lymphocyte to bind with a certain affinity to HLA-peptide complexes present on the surface of the target cell. Reciprocally, soluble HLA-peptide complexes are capable of binding to the TCR present on the surface of T lymphocytes specific to the HLA-peptide complex in question.

At the present time, the system studied most at the molecular level is recognition by CD8+ T lymphocytes of antigenic peptides present in class I major histocompatibility complex (MHC) molecules, and in particular in the HLA-A0201 allele.

In this system, it has been established that the affinity of the TCR for the HLA-peptide complex is very low compared to the affinity of an antibody for its antigen. For this reason, detection of TCR-carrier lymphocytes which are reactive towards a specific peptide in this HLA context with the aid of soluble HLA-A0201 molecules which are charged with peptides and marked is impossible. To overcome this low affinity, Altman et al (1) prepared a multivalent reagent composed of HLA-A0201-peptide complexes where the heavy chain of the HLA is biotinylated, which allows combination as a tetramer with streptavidine. This HLA-peptide tetramer has an increased avidity for the appropriate TCR-carrier T lymphocytes and can therefore be used to visualize reactive populations by immunofluorescence.

However, the TCR is not the only molecule of the T lymphocyte which can interact with the HLA-peptide complex. In fact, during physiological recognition the binding of the TCR to the MHC-peptide complex is intensified by binding of the co-receptor CD8 to a constant portion of class I MHC molecules. The participation of CD8 in the interaction varies from one lymphocyte clone to the other and in some cases can lead to a very significant increase in the capacity for binding to a given HLA-peptide complex. This ability of CD8 to bind to class I HLA consequently leads to a background noise of binding of class I HLA tetramers on the CD8+ T lymphocytes which carry TCR which are non-specific to the HLA-peptide complex. This background noise increases with the concentration of tetramer used and can lead to falsely positive immunofluorescence results. To attempt to reduce this non-specific marking, the majority of teams carry out their marking with class I HLA tetramers in the presence of anti-CD8 antibodies. However, only some anti-CD8 antibodies are effective and the optimum concentration ratios between the antibody and the tetramer must be readjusted for each test. As a result of these disadvantages, detection of specific sub-populations with a low representation within a non-specific population (for example of the order of 0.1 to 1%) becomes difficult.

Another potential application of HLA tetramers has moreover been proposed. This comprises isolation by screening (in flow cytometry or by immunomagnetic screening) of lymphocyte populations which are reactive towards a given HLA-peptide complex for the purpose of in vitro expansion and then therapeutic use within passive anti-viral or anti-tumoral immunization protocols. However, the background noise of binding of the tetramer due to the participation of CD8 may constitute a serious obstacle in this application, since it leads to isolation of an often significant fraction of T lymphocytes which are not reactive with respect to the selecting HLA-peptide complex.

Salter et al (2) have shown that binding of a membrane HLA expressed by cells transfected with a CD8$\alpha\alpha$ co-receptor was modified when the HLA carried a mutation in the $\alpha$3 domain.

Study of such mutations by the inventors has led them to verify that soluble mutated tetramers effectively bind less CD8, regardless of whether $\alpha\alpha$ or $\alpha\beta$, combined or not combined with a TCR on the surface of the T lymphocyte, which manifests itself in a reduction in the background noise.

It is therefore to be expected that the loss in affinity resulting from the mutation leads to a loss in the specific signal which is total or restricted to certain CD8-dependent T lymphocyte clones. In this respect, the article by Salter et al shows that certain CD8-dependent alloreactive clones lose their cytotoxicity with respect to cells carrying mutated HLA-A2, whereas others are less affected.

It would thus be possible that the mutated tetramers detect only a fraction of reactive cells (the less CD8-dependent) within a polyclonal population.

The numerous comparative markings of polyclonal populations with mutated and native tetramers carried out by the inventors by double-marking with an anti-CD8 antibody demonstrate that, on the contrary, the mutated tetramer unexpectedly recognizes the same percentage of specific cells as the native tetramer.

Furthermore, comparison of the marking with the mutated tetramer on a highly CD8-dependent clone and a clone of low CD8 dependency shows a comparable effectiveness of the binding of the tetramer with respect to the intensity of the expression of the TCR.

It thus seems that the mutation very significantly reduces binding of the tetramer to CD8 alone, but affects its binding to the TCR-CD8 complex much less.

The invention therefore lies in the utilization of the properties demonstrated in mutated or, more generally, modified HLA multimers and provides such multimers and their complexes with antigenic peptides, as new products.

It also provides the use of these molecules for the detection and/or isolation of peptide-specific CD8+ T lymphocyte populations.

It additionally provides a method for detection and/or isolation of such populations with the aid of such molecules which are charged with peptide, in particular for applications in diagnostics and therapeutics.

The multimers according to the invention are built up from recombinant protein analogues of class I MHC and are characterized in that the proteins comprise at least one modification in the zone of interaction of a heavy chain of the class I MHC with the CD8 co-receptor of T lymphocytes, leading to a reduction, or even suppression of the affinity of the interaction between the heavy chain and the CD8. The modification of the zone of interaction more specifically relates to the α3 domain of the heavy chain.

More particularly, it is a mutation in the α3 domain of at least one amino acid with respect to the corresponding domain of a native heavy chain which is capable of binding to the said CD8 co-receptor.

There may be mentioned by way of example the mutation of an alanine residue into a valine residue in position 245 of the α3 domain of the HLA-A2 molecule.

SUMMARY OF THE INVENTION

The modification may also consist of a chemical modification of at least one amino acid and/or a deletion of at least one amino acid, this or these types of modification being in addition to one or more mutations, where appropriate.

The invention also provides, as new products, complexes built up from the multimers defined above and antigenic peptides.

In these complexes the multimers are present in particular in the form of tetramers.

According to the invention, these complexes are used for the detection and/or isolation of CD8+ T lymphocyte populations which recognize the antigenic peptide of the complexes in a specific manner.

The use of the complexes defined above enables the background noise of non-specific binding to be reduced very significantly without modifying the specific marking and, in addition, removes the need for conjoint use of an anti-CD8 antibody during immunofluorescence analyses.

In a preferred use, the said complexes are used in a cell screening process, such as immunomagnetic screening.

An immunomagnetic screening technique for isolating specific T lymphocytes in mice is described by Luxembourg et al. (5).

This technique is based on the use of a system of beads coated with MHC-peptide complexes (produced in a Drosophilus system; charged with peptides and chemically biotinylated).

The invention also provides a method for detection and/or isolation of peptide-specific CD8+ T lymphocyte populations from a polyclonal population. The detection method is characterized in that it comprises:
  bringing the polyclonal population into contact with multimers complexed with antigenic peptides as defined above under conditions which allow interaction between the modified class I MHC complexes/peptides and T lymphocyte receptors which have an affinity for the said complexes,
  visualization of lymphocyte populations which are bound to the said complexes.

DETAILED DESCRIPTION OF THE INVENTION

The visualization is carried out, for example, by fluorescence using multimers comprising fluorescent compounds.

The method for isolation of peptide-specific lymphocyte populations from polyclonal populations also falls within the context of the invention and can be used, where appropriate, after the above detection stage.

This method utilizes the immunomagnetic screening technique and is characterized in that it comprises:
  bringing the polyclonal population into contact with magnetic beads on which are bound peptide/class I MHC analogue complexes as defined above under conditions which allow interaction between the said complexes and T lymphocyte receptors which have an affinity for these complexes,
  recovery of the bound populations, the screening operation being repeated, if desired, and/or followed, where appropriate, by a stage
  of in vitro amplification of the selected populations.

The increase in the differential between the background noise and specific marking with the modified multimers as defined above allows better discrimination of specific lymphocyte populations within a polyclonal population, and therefore makes immunomagnetic screening with these multimers very effective.

The MHC molecules comprise, for example, an enzymatic biotinylation moiety on the heavy chain. The beads on which the complexes are bound are coupled to streptavidine.

The polyclonal populations originate from samples taken from patients, such as synovial fluids or mononucleated cells of peripheral blood.

The amplification stage of selected populations is advantageously carried out by polyclonal stimulation under conditions which do not affect the representativeness of the amplified populations. PHA, IL2 or irradiated PBL, for example, are used.

The invention also provides T lymphocyte populations which have been selected and, where appropriate, amplified, characterized in that they are made up exclusively of T lymphocytes which are reactive towards the peptide of a given complex.

Such peptide-specific populations are of great interest in therapeutics, and more specifically for applications which rely on their re-administration in accordance with adoptive immunotherapy.

The invention thus provides pharmaceutical compositions, characterized in that they are developed from a peptide-specific T lymphocyte population as defined above in combination with a pharmaceutical vehicle.

Such compositions can advantageously be administered by injection.

It is thus possible to restore an antiviral or antitumoral immunity after injection of T lymphocytes which recognize, respectively, a defined class I MHC/viral or tumoral peptide complex, or to correct an immunity disequilibrium (for example the case of autoimmunity) by the administration of T cells directed against a given antigen and having activatory or inhibitory properties on the immune response.

Other characteristics and advantages of the invention are given in the examples which follow, which are given purely by way of illustration and in which reference is made to FIGS. 1 to 7, which show, respectively FIGS. 4A and 4B show the results of the marking of these clones.

EXAMPLE 1

Preparation of an HLA-A0201 Tetramer Mutated in the Zone of Interaction with the CD8 Co-receptor A bacterial expression plasmid containing the cDNA which codes for the heavy chain of HLA-A0201, lengthened by a sequence which codes for an enzymatic biotinylation motive was used (construction according to Altman et al (1)). The zone which codes for the α3 domain had been amplified with the specific primers

```
                                      SEQ ID no. 1
5' CCTTCCAGAAGTGGGTGGCTGTGGTGGTGCC 3'
and
                                      SEQ ID no. 2
5' GGCACCACCACAGCCACCCACTTCTGGAAGG 3'
```

A mutation of a base to transform the alanine codon into a valine codon was introduced into the amplification fragments using the Stratagene QuickChange Site-directed Mutagenesis R kit.

The mutated fragment was reintroduced into the expression plasmid and the presence of the mutation was checked by sequencing.

The mutated HLA-A0201 heavy chain had been produced in the bacterial inclusion body and the HLA monomer charged with peptide, and then the corresponding mutated tetramer, could be obtained in accordance with a renaturation protocol previously described by Garboczi et al (3).

EXAMPLE 2

Comparative Study of the Effectiveness and Specificity of Immunofluorescent Marking Between a Native HLA-A0201 Tetramer and the Mutated HLA-A0201 Tetramer Charged with Different Peptides 1) Marking of lymphocyte clones Native HLA-A0201 tetramers and corresponding mutated tetramers were charged either with a peptide originating from the protein BMLF1 of the EBV virus or with a peptide originating from the protein pp 65 of CMV.

The native tetramers are obtained in accordance with the technique of example 1, but without the mutation.

Specific and non-specific clones were marked and used at increasing concentrations.

Figures 1, 1A:
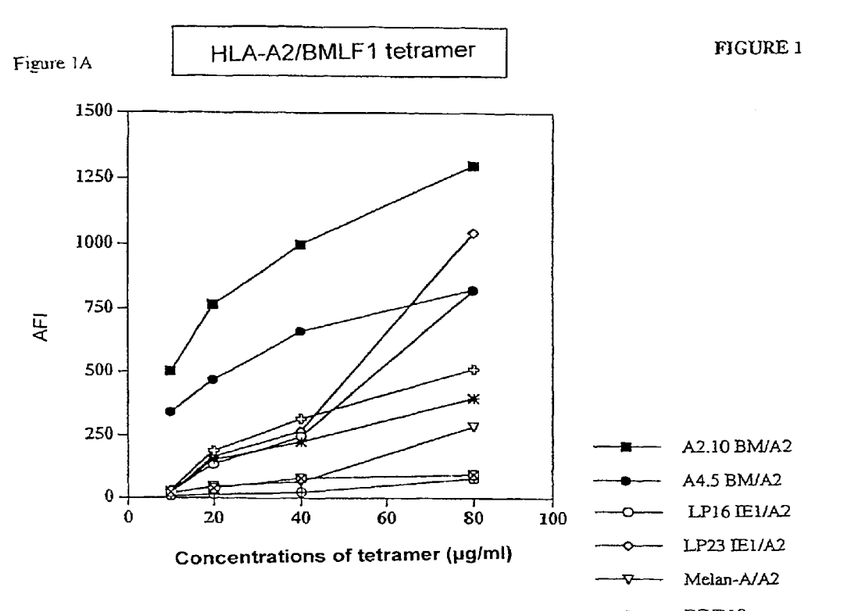
FIGS. 1 and 2 show the fluorescence intensity (averages) as a function of the concentrations of native tetramers (1A, 2A) and of corresponding mutated tetramers (1B, 2B) with tetramers charged with peptide originating from BMLF1 (FIG. 1) or pp65 (FIG. 2)
Figure 1B:
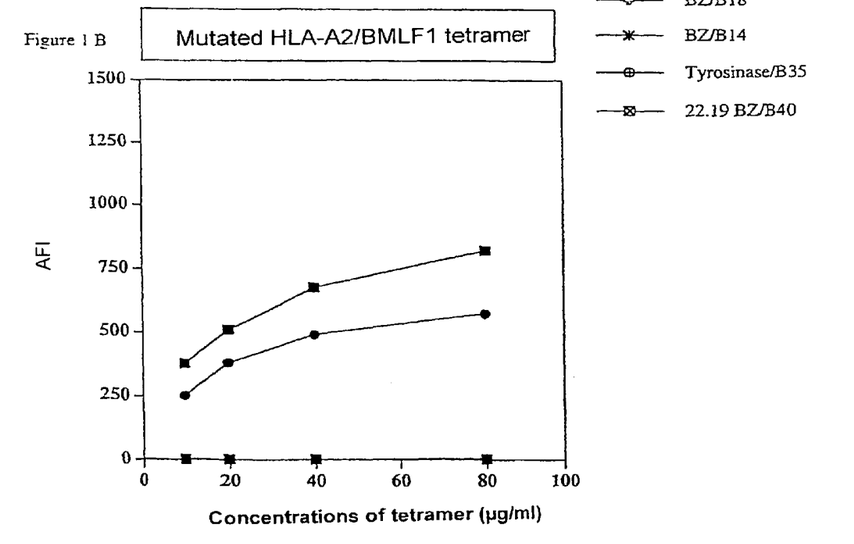

FIG. 1 gives the average fluorescence intensity (AFI) obtained with the native HLA-A2/BMLF1 tetramers (FIG. 1A) and with the corresponding mutated tetramers (FIG. 1B).

It is found that the native HLA-A2/BM tetramer shows a background noise of binding on some non-specific clones which increases with the dose of tetramer used.

This background noise does not seem associated exclusively with the HLA restriction of the clone in question, but also depends on the peptide charged, since two HLA-A0201-restricted anti-IE1 clones give a high background noise, whereas the similarly HLA-A0201-restricted anti-melan-A clone gives a moderated background noise.

With the mutated tetramer, the averages of the fluorescence (AFI) obtained on the specific clones (BM/A2) are lower than those obtained with the native tetramer, but the background noise on the non-specific clones is virtually zero, regardless of the concentration of tetramer used.

Figures 2, 2A, 2B:
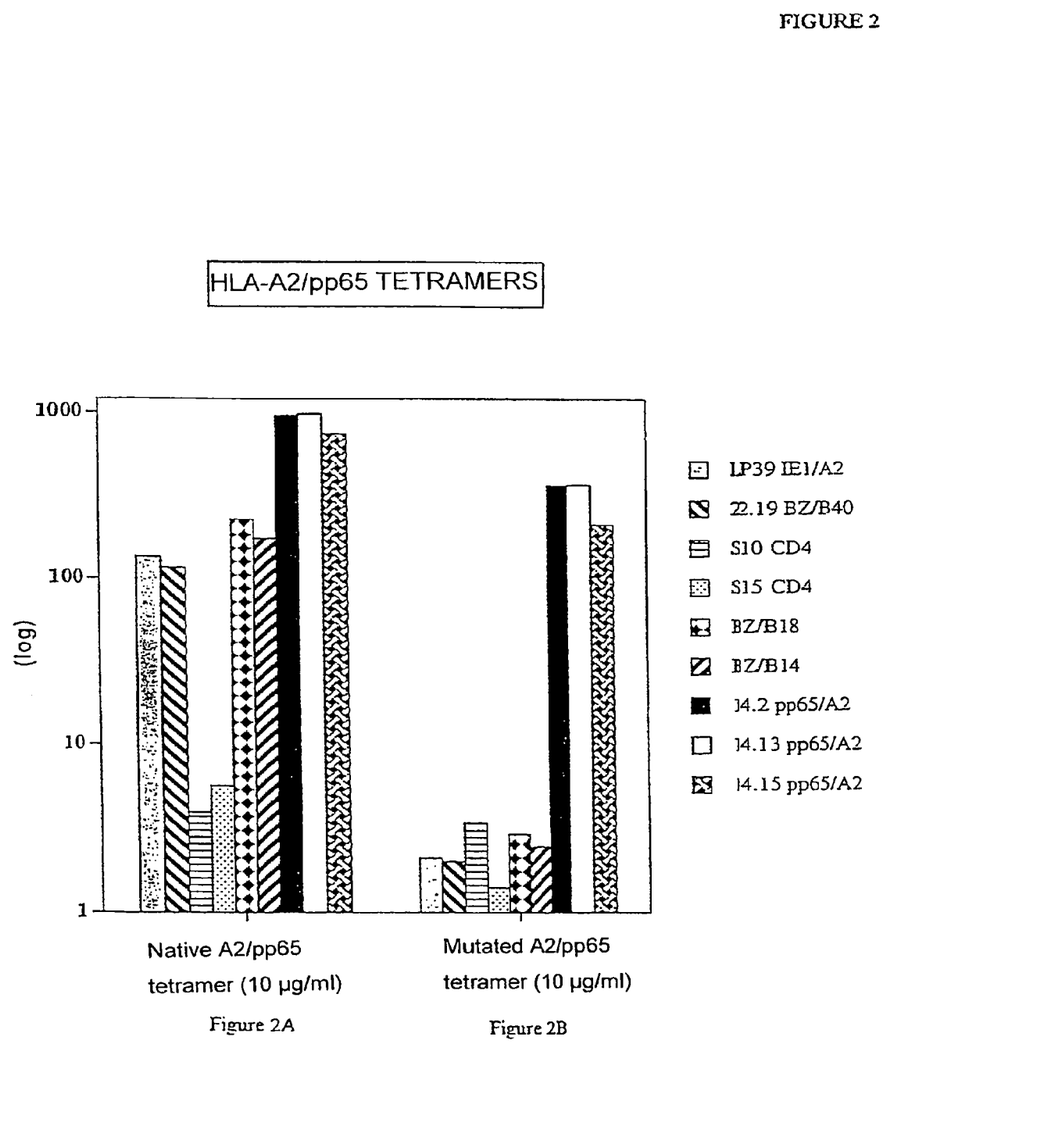

It can be seen that this difference in background noise between the native tetramer and the mutated tetramer is not peculiar to the A2/BM tetramer, since it is also observed with the HLA-A2/pp 65 tetramer (see FIG. 2).

In this FIG. 2, the average fluorescence is indicated on a log scale in order to visualize the low background noise of marking obtained with the mutated tetramer. It is found that the differential between the specific marking and the non-specific marking is of the order of 2 $\log(10^2)$ with the mutated A2/pp 65 tetramer, whereas it is only 1 log with the native tetramer. The two notable exceptions are the two anti-EBV CD4 clones, for which the background noise is very low with the native tetramer. This observation supports the hypothesis according to which the background noise of marking obtained with the native tetramer is due to a certain percentage of non-specific binding of the tetramer to CD8.

Figure 3:
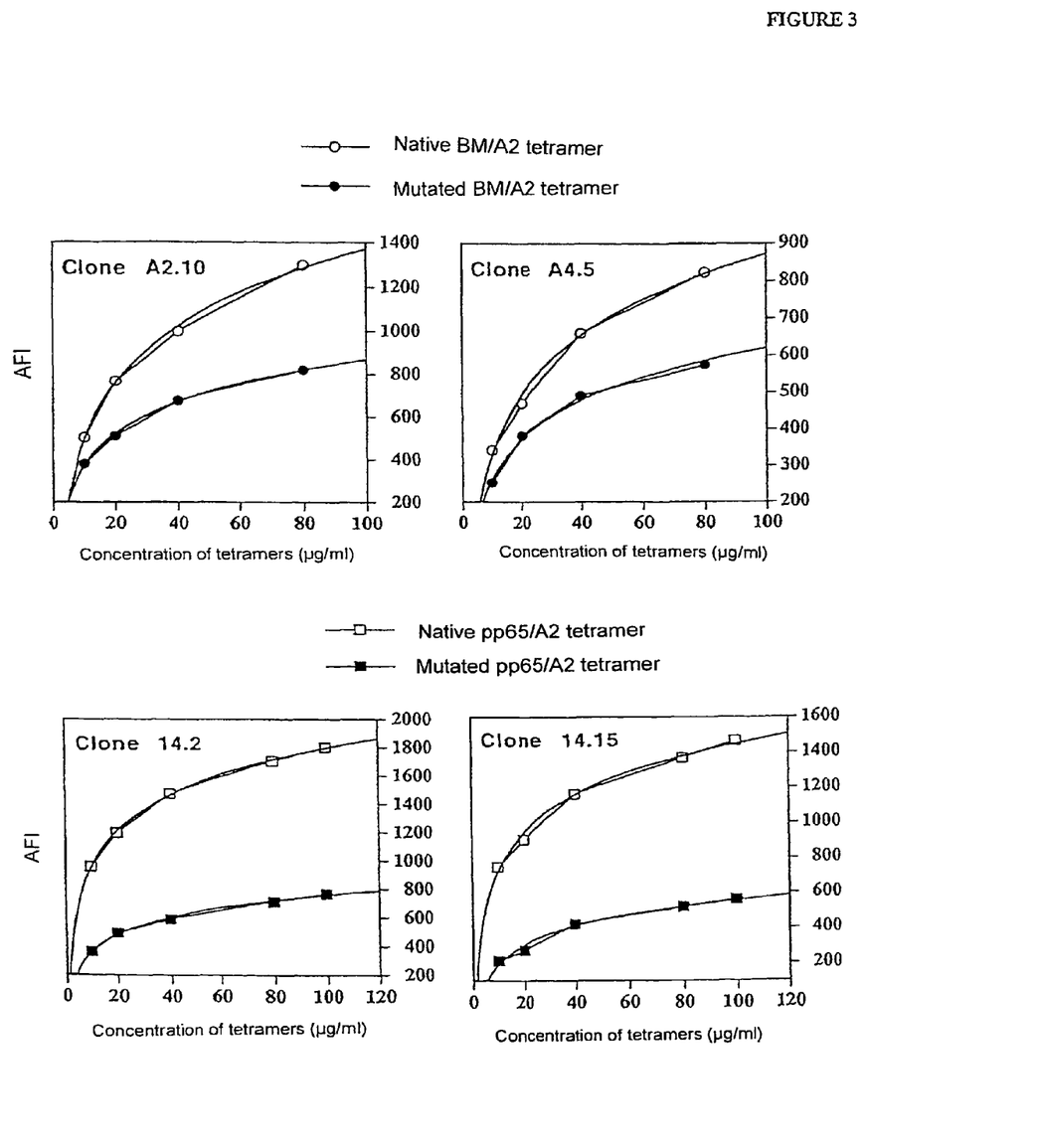
FIG. 3 shows the average fluorescence intensities as a function of the concentrations of native and mutated tetramers with specific clones.

FIG. 3 shows the marking differences obtained with the mutated and native tetramers charged with pp 65 on specific clones. The difference between the saturation curves obtained with the mutated tetramer and the native tetramer show that there is a greater number of binding sites for the native tetramer than for the mutated tetramer on these clones: it is therefore highly probable that in the case of the native tetramer some valencies interact with the CD8 alone, especially since this molecule is expressed at a greatly higher density than that of TCR on the surface of the T lymphocyte.

Other experiments have been carried out to test whether the specific marking with the mutated tetramer was affected significantly by the degree of CD8-dependence of specific clones. In fact, it is well-known that among the T CD8+ clones, some clones have a high need of CD8 to intensify the specific interaction between their TCR and the HLA-peptide complex, while other clones dispense with it.

The degree of CD8 dependency was estimated by the cytotoxicity test of Couedel et al (4) with or without anti-CD8 antibodies and is regarded as inversely proportional to the affinity of the TCR for the HLA-peptide complex.

Figure 4A:
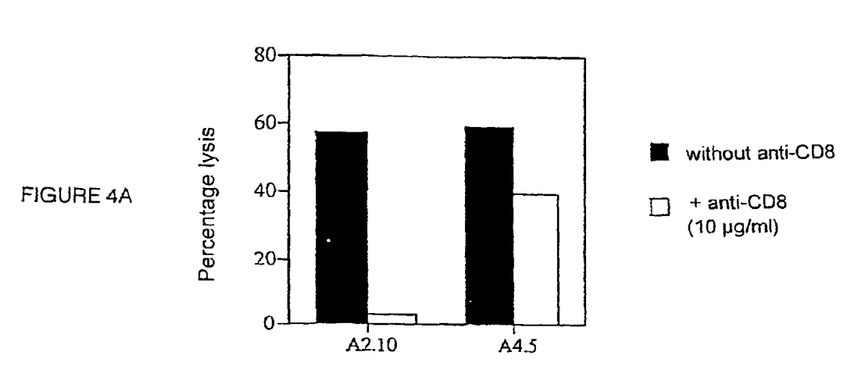
FIG. 4A shows the percentage of lysis, with or without anti-CD8 antibodies, of 2 specific clones of a B HLA-A0201 line charged with a BMLF1 peptide.

FIG. 4A shows a test of cytotoxicity against an HLA-A0201 line charged with BMLF1 peptide (10 μM) with two specific clones. The clone A2.10 is highly CD8-dependent since its cytotoxicity is annulled by the anti-CD8 antibody, whereas the A4.5 clone has a relatively low CD8 dependency.

Figure 4B:
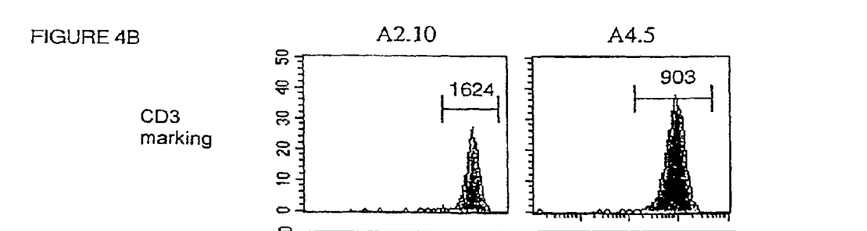
Figure 4C:
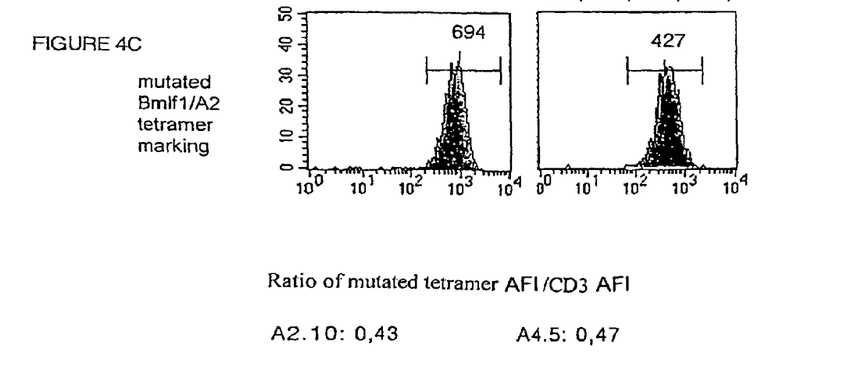

Marking with the mutated tetramer and marking with an anti-CD3 antibody was carried out to estimate the number of TCR expressed on the surface. The results are given in FIGS. 4B (CD3 marking) and 4C (marking with the mutated BMFL1/A2 tetramer).

It is found that the ratio of tetramer marking/CD3 marking is very comparable for the two clones, which indicates that marking with the mutated tetramer is affected little by the degree of CD8 dependency (and thus, by inference, by the TCR affinity).

The reduction in the affinity for CD8 induced by the mutation of the HLA molecule thus does not significantly affect the specific marking of the tetramer.

b) Detection of specific cells within a polyclonal population

To compare the ability of the native and mutated tetramer to detect a small percentage of specific cells within a polyclonal population, peripheral lymphocytes from two HLA-A0201 patients (designated A and B below) were marked. These are patients in whom an anti-CMV pp 65 peptide response was demonstrated beforehand. These lymphocytes were amplified by polyclonal methods in vitro beforehand and frozen.

Figure 5:
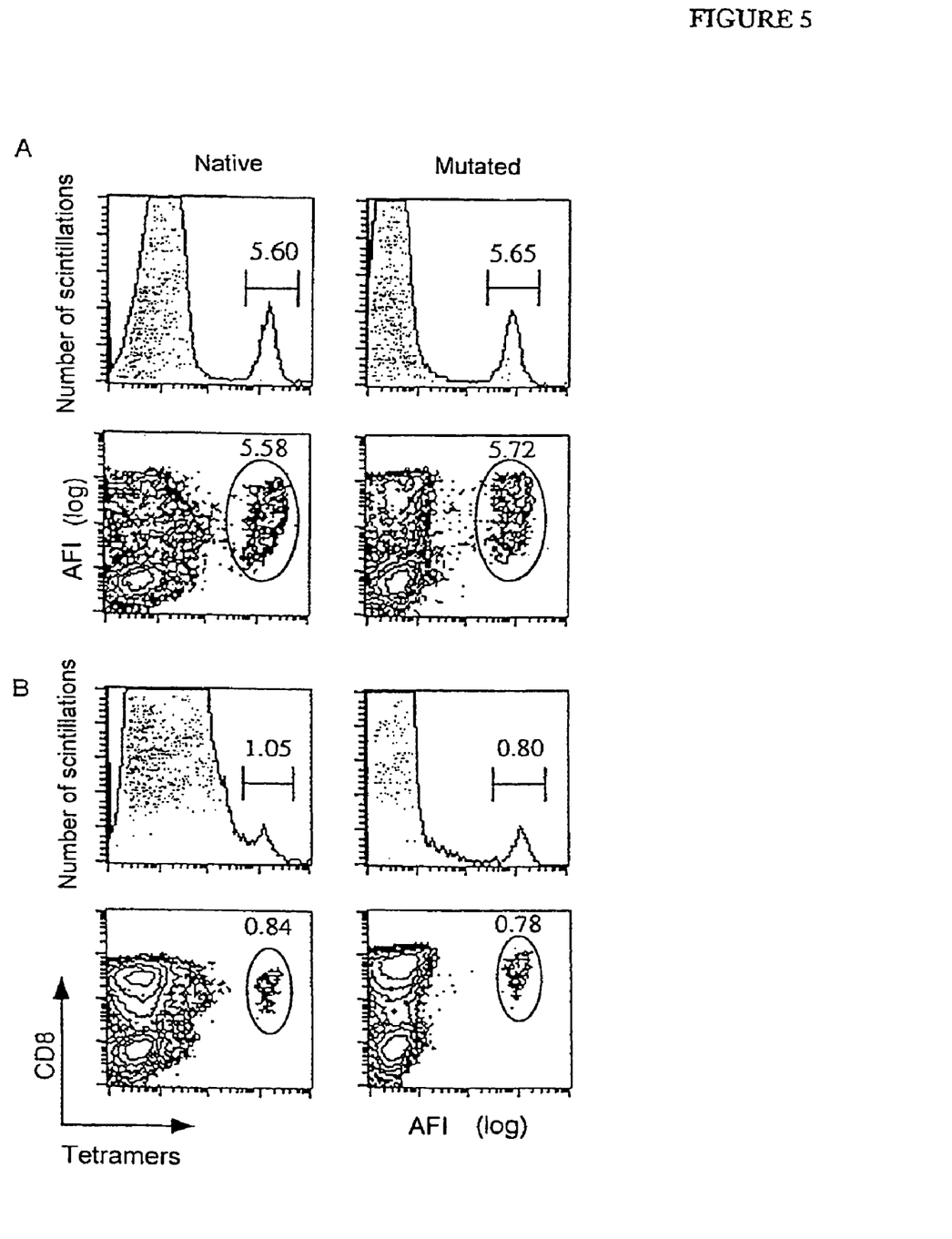
FIG. 5 shows the results of single (with phycoerythrin, PE) and double (PE and marked anti-CD8 antibodies) marking of native and mutated tetramers with the lymphocytes of 2 patients

The results obtained for patients A and B are shown in FIG. 5, FIG. 5A corresponding to patient A and FIG. 5B to patient B. They are the results of single marking of HLA-A0201/pp 65 tetramers with phycoerythrin in an amount of 20 μg/ml and corresponding double marking (tetramers marked with PE and anti-CD8 antibodies marked with FITC). This figure also gives the average fluorescence intensity (log).

Firstly, it is found that the discrimination ability of the native tetramer with single marking varies according to the percentage of specific cells in the starting population. In fact, for patient A, the peak of positive cells, which represents 5.60%, is easily identifiable, whereas for patient B this peak is contaminated by non-specific marking, which renders it difficult to determine the percentage of positive cells. In agreement with the literature, double marking of native tetramer and anti-CD8 reduces the background noise and therefore allows clear identification of the positive sub-population and precise estimation of its percentage (0.84% in this case). This thus shows that precise estimation of the percentage of positive cells with the native tetramer involves the use of double marking with anti-CD8.

On the other hand, single marking with the mutated tetramer allows identification without ambiguity of a peak of positive cells in the two patients. The percentages of positive cells obtained are virtually identical to those obtained with double marking with the native tetramer. This demonstrates that all the specific cells which can be detected by the native tetramer are also detectable with the mutated tetramer, and thus corroborates the results obtained with the clones of high CD8 and low CD8 dependency, that is to say the mutation does not significantly affect the specific recognition.

Furthermore, these results show that the double marking with the mutated tetramer does not provide new elements with respect to single marking. Finally, it can be seen that the averages of the fluorescence obtained with the anti-CD8 antibodies with double marking with the native tetramer (216 and 193 for patients A and B) are significantly lower than those obtained with double marking with the mutated tetramer (366 and 370 for patients A and B). The averages of the fluorescence obtained after single marking of the total population with anti-CD8 were, respectively, 340 and 355 for patients A and B. This demonstrates the binding competition between the anti-CD8 antibody and the native tetramer, competition which does not result with the mutated tetramer.

The use of the mutated tetramer thus allows double marking with anti-CD8 to estimate the percentage of specific cells within a polyclonal population to be dispensed with.

EXAMPLE 3

Comparative Study of the Effectiveness and Specificity of Immunomagnetic Screening Carried Out with the Native HLA-A0201 Tetramer and the Mutated HLA-A0201 Tetramer Charged with the Peptide p65

Biotinylated HLV-A0201 monomers charged with peptide pp65 were bound to magnetic beads coupled to streptavidine (DYNABEADS M-280 Streptavidine, DYNAL). The lymphocyte populations used in the study originated from the synovial fluids or PBL of patients suffering from rheumatoid polyarthritis or PBL originating from healthy donors seropositive in respect of CMV.

Figure 6:
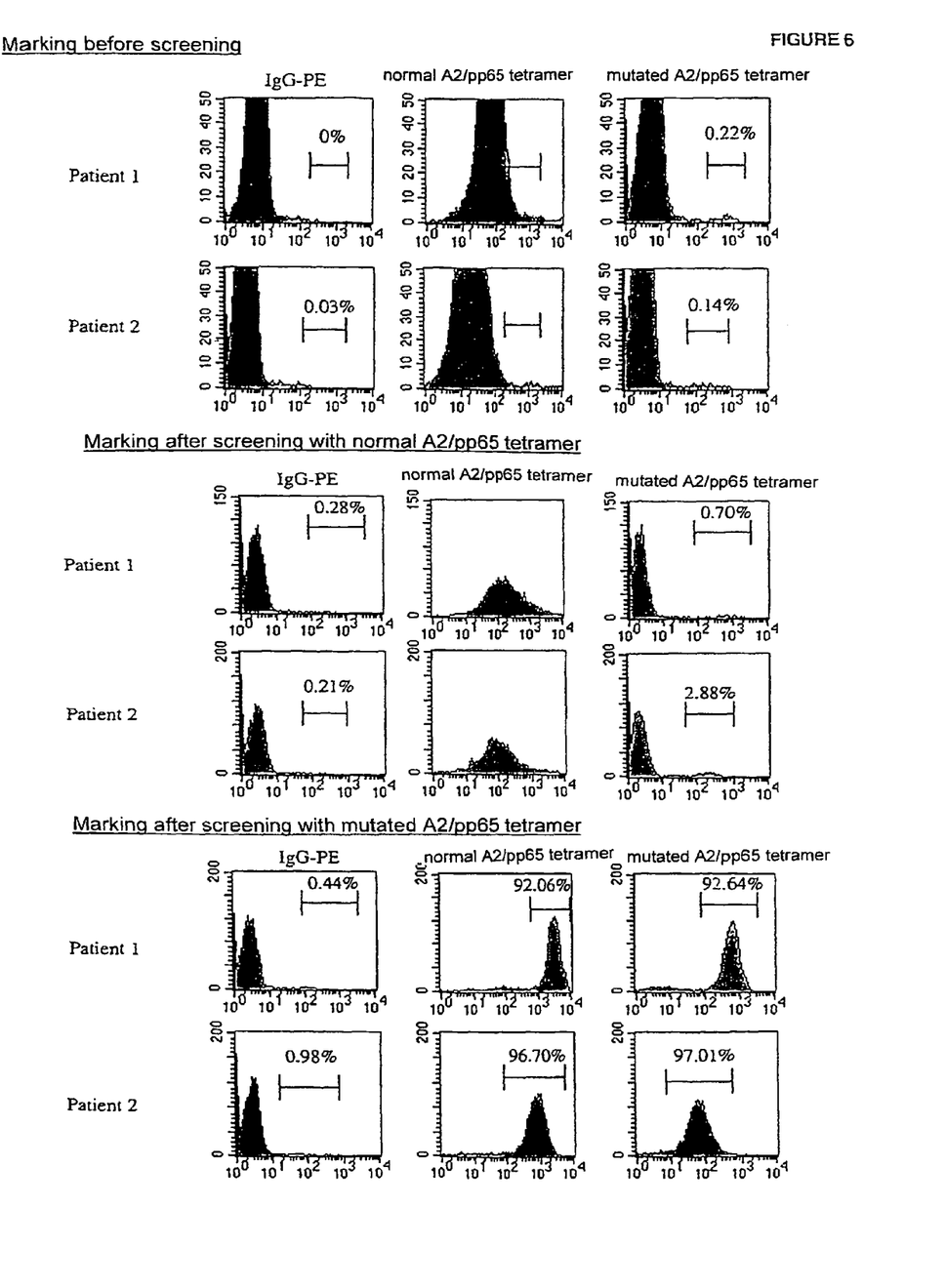
FIGS. 6 and 7 show the results of immunomagnetic screening carried out with native tetramers and mutated tetramers.

The results of single marking with the native tetramer and the mutated tetramer on these polyclonal populations are shown in FIG. 6. With the mutated tetramer it is possible to demonstrate a low percentage of positive cells in the two samples (0.22% and 0.14%), positive cells which are virtually unidentifiable with the native tetramer.

These populations were subjected to screening with beads charged either with the native tetramer or with the mutated tetramer, and the populations selected were then amplified in vitro by polyclonal stimulation (PHA, IL2, irradiated PBL), a stimulation which does not affect the representativeness of the amplified populations.

Marking was then carried out on these populations which had been screened and amplified with the two tetramers.

As shown in FIG. 6, the cells originating from screening with the native tetramer are marked positively with this same tetramer, but on the other hand a very low percentage of these cells are positive with the mutated tetramer (0.7% and 2.88%).

The results are remarkably different after screening with the mutated tetramer, since the populations which have been screened are highly positive with the two tetramers.

The concentration factor of positive cells obtained with the mutated tetramer is 421 for sample 1 (92.64% v. 0.22%) and 693 for sample 2 (97.01% v. 0.14%).

These results show that by screening with the mutated tetramer, it is possible to obtain a pure positive population of more than 90% from a sample in which this population represents 0.1 to 0.2%.

The general nature of this observation is illustrated by the table below, which describes the results of the screening carried out with the native tetramer and the mutated tetramer starting from PBL and synovial lymphocytes of patients and healthy donors.

| | | % of positive cells of tetramers (concentration factor) | | | |
|---|---|---|---|---|---|
| | Not | First screening with | | Second screening with | |
| Samples | screened | A2/pp65 native | A2/pp65 mutated | A2/pp65 native | A2/pp65 mutated |
| SFL 1 | 14.0 | 95.0 (6.8) | | | |
| PBL 1 | 5.6 | 89.5 (16.0) | 97.9 (17.5) | | |
| SFL 2 | 1.4 | 25.3 (18.1) | | 75.9 (3.0) | |
| PBL 2 | 0.8 | 51.1 (63.9) | 97.5 (121.9) | | |
| SFL 3 | 0.6 | 13.7 (22.8) | | | |
| PBL 3 | nd | 8.5 (nd) | | 12.0 (1.4) | |
| SFL 4 | 0.3 | 4.1 (13.6) | | 8.6 (2.1) | |
| SFL 5 | 0.2 | 0.7 (3.5) | 92.5 (462.5) | | |
| SFL 6 | 0.14 | 2.9 (20.6) | 97.1 (693.6) | | |
| PBL 4 | 0.00 | | 82.9 (921.1) | | |
| PBL 5 | 0.02 | 0.04 (2.0) | 2.2 (110.0) | | 98.7 (44.90) |

By carrying out repeated screening with the mutated tetramer, it is possible to obtain pure specific populations from sub-populations which are even less frequent (cf. PBL5 in the table). On the other hand, this result is much more difficult to obtain with the native tetramer; it seems in fact that the non-specific cells isolated by a first screening with the native tetramer had an affinity sufficient to be selected again during the subsequent screening. Very mediocre concentration factors are thus arrived at by carrying out a second screening (cf. PBL3 and SFL4).

Another study related to the reactivity of populations which had been subjected to screening to verify that the cells selected for their ability to bind the mutated A2/pp 65 tetramer were certainly reactive with respect to this HLA-peptide complex in a physiological context.

To this effect, the activation of screened lymphocyte populations, objectified by induction on the surface of the a chain of the receptor for IL2 (CD25), after placing in the presence of T2 cells (A0201+) charged with peptide pp 65, was studied.

All of these results demonstrate the manifest superiority of the mutated tetramer with respect to the native tetramer for selection by immunomagnetic screening of populations with a low representation in the starting population.

If the specific populations are more numerous in the starting sample, it thus becomes possible to isolate reactive cells with the native tetramer, but the degrees of purity of the populations obtained are much lower than those obtained in parallel with the mutated tetramer (table).

BIBLIOGRAPHY REFERENCES

1) Altman J. D. et al, 1996, Science 274:94-6 and U.S. Pat. No. 5,635,363
2) Salter, R. D. et al, 1990, Nature 345:41-46
3) Garboczi D. N. et al, 1992, Proc Natl Acad Sci USA 89:3429-33
4) Couedel, C., M. et al, 1999, J. Immunol 162-6351-B.
5) Luxembourg A. T. et al, Nature Biotechnology, vol. 16, March 1998, 281-285

SEQUENCE LISTING

```
<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Description of the artificial sequence:
      homologous region to a part of human HLA-A0201 gene

<400> SEQUENCE: 1
ccttccagaa gtgggtggct gtggtggtgc c                              31

<210> SEQ ID NO 2
<211> LENGTH: 31
<212> TYPE: DNA
<213> ORGANISM: Artificial Sequence
<220> FEATURE:
<223> OTHER INFORMATION: Description of the artificial sequence:
      homologous region to a part of human HLA-A0201 gene

<400> SEQUENCE: 2
ggcaccacca cagccaccca cttctggaag g                              31
```

Figure 7:
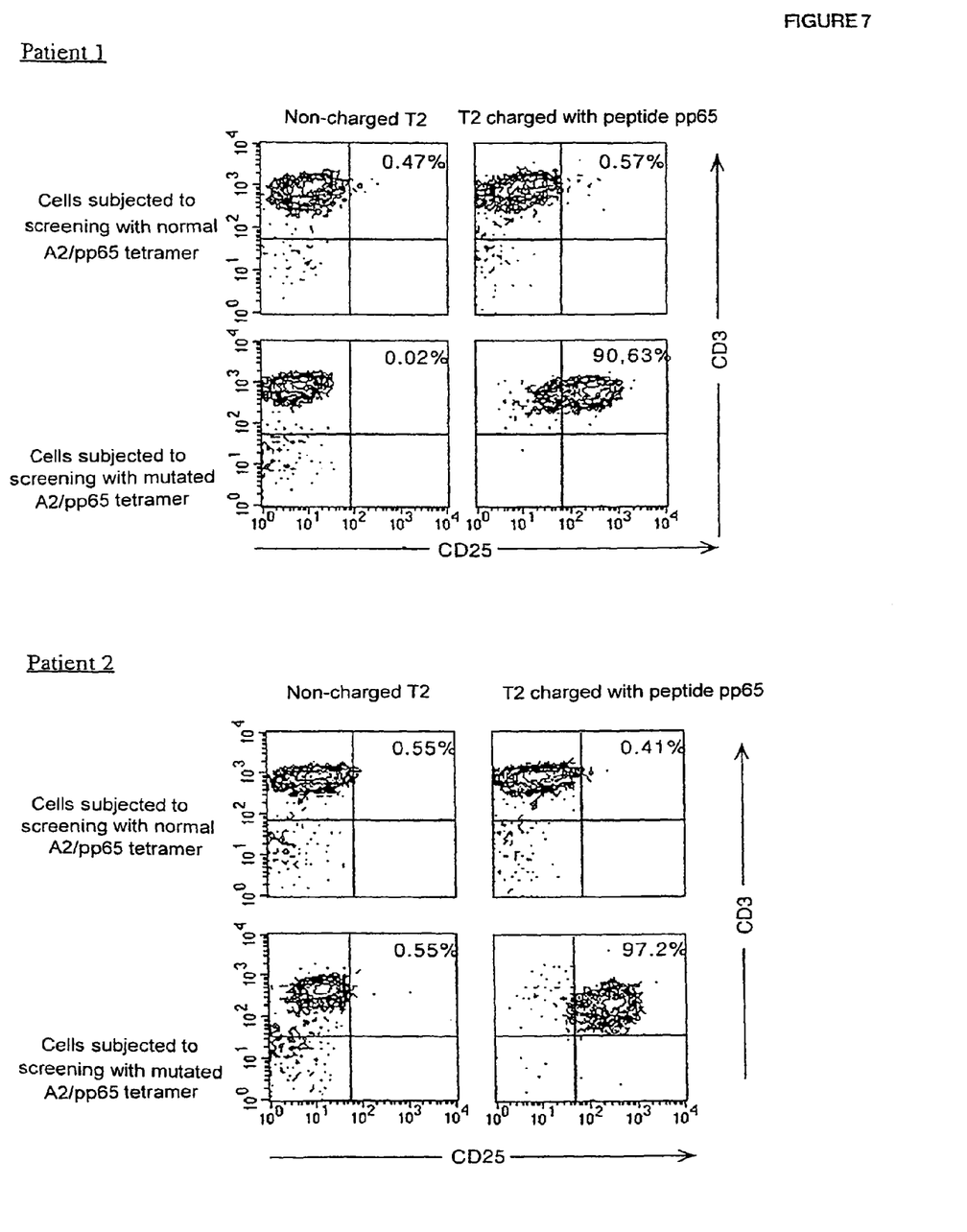

As shown in FIG. 7, the populations which had been screened using the native tetramer do not express CD25 after contact with T2 cells charged with peptides.

On the other hand, the majority of these cells which have been screened with the mutated tetramer become activated in the presence of T2 charged with the peptide pp 65 and the percentage of CD25-positive cells corresponds well with the percentage of cells which were marked by the mutated tetramer (90.63% of activated cells v. 92.64% of marked cells and 97.20% v. 97.01% for patients 1 and 2 respectively).

These results demonstrate that the cells marked and screened with the mutated tetramer are exclusively reactive cells, whereas the cells screened with the native tetramer are non-reactive.

The fact that no reactive cell is found after screening with the native tetramer whereas a distinction between some positive cells in this population was achieved is probably due to too low a percentage of these cells for them to be detectable in a functional test.

The invention claimed is:

1. A method of detecting a specific CD8+T lymphocyte from a polyclonal T lymphocyte population obtained from a biological sample, said method comprising:
   (a) incubating the polyclonal T lymphocyte population, wherein each member of the polyclonal population comprises a T cell receptor molecule and a CD8 co-receptor molecule, with a multimer of class I MHC molecules, the multimer of class I MHC molecules comprising:
      (i) a streptavidin molecule;
      (ii) a plurality of modified HLA-A2 heavy chain molecules, said modified HLA-A2 heavy chain molecules having an alanine to valine substitution at amino acid position 245 in the α3 domain of each of the HLA-A2 heavy chain molecules, wherein each HLA-A2 heavy chain molecule is coupled to a biotin molecule and the biotin molecule is bound to the streptavidin molecule;

(iii) a particular antigenic peptide that is specifically recognized by the T cell receptor molecule of the specific CD8+T lymphocyte; and (iv) beta-2 micro globulin; and (b) detecting the specific binding of the specific CD8+T lymphocyte to the multimer of class I MHC molecules.

2. The method of claim 1, wherein the biological sample is synovial fluid.

3. The method of claim 1, wherein the biological sample is mononucleated cells of peripheral blood.

4. The method of claim 1, wherein the multimer of class I MHC is a tetramer.

5. The method of claim 1, wherein the streptavidin is further coupled to magnetic beads.

6. The method of claim 1, wherein the multimer of class I MHC molecules further comprises a fluorescent compound.

7. The method of claim 6, wherein the fluorescent compound is phycoerythrin.

8. The method of claim 1, wherein the detecting is carried out by flow cytometry.

9. A method of isolating a specific CD8+T lymphocyte from a polyclonal T lymphocyte population obtained from a biological sample, said method comprising:

(a) incubating the polyclonal T lymphocyte population, wherein each member of the polyclonal population comprises a T cell receptor molecule and a CD8 co-receptor molecule, with a multimer of class I MHC molecules, the multimer of class I MHC molecules comprising:

(i) a streptavidin molecule;

(ii) a plurality of modified HLA-A2 heavy chain molecules, said HLA-A2 heavy chain molecules having an alanine to valine substitution at amino acid position 245 in the α3 domain of each of the HLA-A2 heavy chain molecules, wherein each HLA-A2 molecule is coupled to a biotin molecule and the biotin molecule is bound to the streptavidin molecule;

(iii) an MHC-binding peptide that specifically interacts with the T cell receptor molecule of the specific CD8+T lymphocyte; and (iv) beta-2 microglobulin; and (b) detecting the specific binding of the specific CD8+T lymphocyte to the multimer of class I MHC molecules;

(c) recovering the bound specific CD8+T lymphocyte; and, optionally, (d) amplifying the recovered CD8+T lymphocyte.

10. The method of claim 9, wherein the multimer of class I MHC is a tetramer.

11. The method of claim 9, wherein the streptavidin is further coupled to magnetic beads.

12. The method of claim 9, wherein the multimer of class I MHC molecules further comprises a fluorescent compound.

13. The method of claim 12, wherein the fluorescent compound is phycoerythrin.

14. The method of claim 9, wherein the detecting is carried out by flow cytometry.

\* \* \* \* \*

UNITED STATES PATENT AND TRADEMARK OFFICE
CERTIFICATE OF CORRECTION

PATENT NO. : 8,309,312 B2  
APPLICATION NO. : 12/571942  
DATED : November 13, 2012  
INVENTOR(S) : Lang et al.

Page 1 of 1

It is certified that error appears in the above-identified patent and that said Letters Patent is hereby corrected as shown below:

In the Specification

The heading "SUMMARY OF THE INVENTION" located at Col. 3, line 15 should be moved to Col. 2, line 39 before the paragraph starting with "The numerous comparative"

The heading "DETAILED DESCRIPTION OF THE INVENTION" located at Col. 3, line 55 should be moved to Col. 2, line 64 before the paragraph starting with "The multimers according"

Signed and Sealed this  
Seventh Day of April, 2015

Michelle K. Lee  
*Director of the United States Patent and Trademark Office*